United States Patent
Mo et al.

(10) Patent No.: US 11,103,221 B2
(45) Date of Patent: Aug. 31, 2021

(54) SYSTEM AND METHOD FOR PROVIDING VARIABLE ULTRASOUND ARRAY PROCESSING IN A POST-STORAGE MODE

(71) Applicant: Shenzhen Mindray Bio-Medical Electronics Co., Ltd., Shenzhen (CN)

(72) Inventors: Larry Y. L. Mo, San Ramon, CA (US); Glen W. McLaughlin, San Carlos, CA (US); Brian Derek DeBusschere, Orinda, CA (US); Ting-Lan Ji, San Jose, CA (US); Albert Gee, Los Altos, CA (US); David J. Napolitano, Pleasanton, CA (US); Ching-Hua Chou, Mountain View, CA (US); Robert W. Steins, San Clara, CA (US)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 290 days.

(21) Appl. No.: 16/015,581

(22) Filed: Jun. 22, 2018

(65) Prior Publication Data
US 2018/0368813 A1    Dec. 27, 2018

Related U.S. Application Data

(63) Continuation of application No. 14/748,084, filed on Jun. 23, 2015, now Pat. No. 10,085,724, which is a
(Continued)

(51) Int. Cl.
*A61B 8/00* (2006.01)
*A61B 8/08* (2006.01)
(Continued)

(52) U.S. Cl.
CPC .............. *A61B 8/565* (2013.01); *A61B 8/00* (2013.01); *A61B 8/08* (2013.01); *A61B 8/0891* (2013.01);
(Continued)

(58) Field of Classification Search
CPC .. A61B 8/565; A61B 8/08; A61B 8/14; A61B 8/4483; A61B 8/463; A61B 8/5223;
(Continued)

(56) References Cited

U.S. PATENT DOCUMENTS

| 4,265,126 A | 5/1981 | Papadofrangakis |
| 4,604,697 A | 8/1986 | Luthra et al. |

(Continued)

FOREIGN PATENT DOCUMENTS

WO    2008051738 A2    5/2008

OTHER PUBLICATIONS

Anderson, M.E., et al., "The Impact of Sound Speed Errors on Medical Ultrasound Imaging", J. Acous. Soc. of Am., Jun. 2000, pp. 3540-3548, vol. 107, No. 6.
(Continued)

*Primary Examiner* — Peter Luong
(74) *Attorney, Agent, or Firm* — Kory D. Christensen

(57) ABSTRACT

An ultrasonic imaging method includes activating a transmit aperture within a multi-element transducer array, transmitting one or more ultrasonic beams along scan direction(s) that span the region of interest, for each transmit event, receiving ultrasound echoes from each element of a receive aperture, grouping the receive channel echo data into two or more sets corresponding to different receive sub-apertures, combining each sub-aperture data set to generate partially focused echo-location data for one or more reconstruction lines, and storing all the sub-aperture echo data sets during a storage period in a format that can be retrieved for later analysis. A method includes, during a post-storage period, retrieving stored sub-aperture data, combining the sub-aperture data to form one or more selected reconstruction lines, processing echo data to extract motion information from one or more sample positions along the selected
(Continued)

reconstruction lines, and displaying an image representative of the processed motion information.

20 Claims, 5 Drawing Sheets

Related U.S. Application Data continuation of application No. 12/340,578, filed on Dec. 19, 2008, now Pat. No. 9,060,669.

(60) Provisional application No. 61/015,632, filed on Dec. 20, 2007.

(51) Int. Cl.
    *G01S 15/89*     (2006.01)
    *G01S 7/52*     (2006.01)
    *A61B 8/14*     (2006.01)

(52) U.S. Cl.
    CPC .............. *A61B 8/14* (2013.01); *A61B 8/4483* (2013.01); *A61B 8/463* (2013.01); *A61B 8/488* (2013.01); *A61B 8/5207* (2013.01); *A61B 8/5223* (2013.01); *A61B 8/54* (2013.01); *G01S 7/52034* (2013.01); *G01S 7/52049* (2013.01); *G01S 15/8927* (2013.01); *G01S 15/8979* (2013.01); *A61B 8/4488* (2013.01)

(58) Field of Classification Search
    CPC ......... A61B 8/54; A61B 8/0891; A61B 8/488; A61B 8/5207; A61B 8/00; A61B 8/4488; G01S 15/8979; G01S 15/8927; G01S 7/52034; G01S 7/52049
    See application file for complete search history.

(56) References Cited

U.S. PATENT DOCUMENTS

| | | | |
|---|---|---|---|
| 4,852,576 A | 8/1989 | Inbar et al. |
| 4,852,577 A | 8/1989 | Smith et al. |
| 5,161,535 A | 11/1992 | Short et al. |
| 5,260,871 A | 11/1993 | Goldberg |
| 5,269,289 A | 12/1993 | Takehana et al. |
| 5,313,948 A | 5/1994 | Murashita et al. |
| 5,357,962 A | 10/1994 | Green |
| 5,357,965 A | 10/1994 | Hall et al. |
| 5,365,929 A | 11/1994 | Peterson |
| 5,409,010 A | 4/1995 | Beach et al. |
| 5,415,173 A | 5/1995 | Miwa et al. |
| 5,417,215 A | 5/1995 | Evans et al. |
| 5,555,534 A | 9/1996 | Maslak |
| 5,566,674 A | 10/1996 | Weng |
| 5,579,768 A | 12/1996 | Klesenski |
| 5,581,517 A | 12/1996 | Gee et al. |
| 5,617,862 A | 4/1997 | Cole |
| 5,623,928 A | 4/1997 | Wright et al. |
| 5,638,820 A | 6/1997 | Chen |
| 5,654,509 A | 8/1997 | Miele et al. |
| 5,690,111 A | 11/1997 | Tsujino |
| 5,720,289 A | 2/1998 | Wright et al. |
| 5,776,063 A | 7/1998 | Dittrich et al. |
| 5,782,766 A | 7/1998 | Weng et al. |
| 5,799,111 A | 8/1998 | Guissin |
| 5,857,973 A | 1/1999 | Ma et al. |
| 5,871,019 A | 2/1999 | Belohlavek |
| 5,935,074 A | 8/1999 | Mo et al. |
| 5,954,653 A | 9/1999 | Hatfield et al. |
| 5,984,870 A | 11/1999 | Giger et al. |
| 5,993,393 A | 11/1999 | Ryan |
| 6,016,285 A | 1/2000 | Wright et al. |
| 6,036,643 A | 3/2000 | Criton et al. |
| 6,042,545 A | 3/2000 | Hossack |
| 6,068,598 A | 5/2000 | Pan et al. |
| 6,069,593 A | 5/2000 | Lebby et al. |
| 6,102,859 A | 8/2000 | Mo |
| 6,110,119 A | 8/2000 | Hall |
| 6,113,544 A | 9/2000 | Mo |
| 6,120,446 A | 9/2000 | Ji et al. |
| 6,142,943 A | 11/2000 | Mo et al. |
| 6,162,176 A | 12/2000 | Washburn et al. |
| 6,193,663 B1 | 2/2001 | Napolitano et al. |
| 6,221,020 B1 | 4/2001 | Lysyansky et al. |
| 6,263,094 B1 | 7/2001 | Rosich et al. |
| 6,312,385 B1 | 11/2001 | Mo et al. |
| 6,315,728 B1 | 11/2001 | Muzilla et al. |
| 6,322,509 B1 | 11/2001 | Pan et al. |
| 6,358,205 B1 | 3/2002 | Ustener et al. |
| 6,390,983 B1 | 5/2002 | Mo et al. |
| 6,398,733 B1 | 6/2002 | Simopoulos et al. |
| 6,423,003 B1 | 7/2002 | Ustener et al. |
| 6,434,262 B2 | 8/2002 | Wang |
| 6,450,959 B1 | 9/2002 | Mo et al. |
| 6,464,637 B1 | 10/2002 | Criton et al. |
| 6,464,640 B1 | 10/2002 | Guracar et al. |
| 6,464,641 B1 | 10/2002 | Pan et al. |
| 6,468,218 B1 | 10/2002 | Chen et al. |
| 6,491,636 B2 | 12/2002 | Chenal et al. |
| 6,497,661 B1 | 12/2002 | Brock-Fisher |
| 6,503,203 B1 | 1/2003 | Rafter et al. |
| 6,512,854 B1 | 1/2003 | Mucci et al. |
| 6,547,737 B2 | 4/2003 | Njemanze |
| 6,577,967 B2 | 6/2003 | Mo et al. |
| 6,679,847 B1 | 1/2004 | Robinson et al. |
| 6,860,854 B2 | 3/2005 | Robinson et al. |
| 6,926,671 B2 | 8/2005 | Azuma et al. |
| 6,932,770 B2 | 8/2005 | Hastings et al. |
| 6,980,419 B2 | 12/2005 | Smith et al. |
| 7,022,075 B2 | 4/2006 | Grunwald et al. |
| 7,627,386 B2 | 12/2009 | Mo et al. |
| 8,002,705 B1 | 8/2011 | Napolitano et al. |
| 8,784,318 B1 | 7/2014 | Napolitano et al. |
| 9,060,669 B1 | 6/2015 | Mo |
| 2004/0068188 A1* | 4/2004 | Robinson ............ G01S 15/8977 600/447 |
| 2004/0179332 A1 | 9/2004 | Smith et al. |
| 2006/0074320 A1 | 4/2006 | Yoo et al. |
| 2006/0106309 A1* | 5/2006 | Liu ..................... G01S 15/8925 600/447 |
| 2006/0079778 A1 | 7/2006 | Mo et al. |
| 2008/0146922 A1 | 6/2008 | Steins et al. |
| 2010/0189329 A1 | 7/2010 | Mo et al. |

OTHER PUBLICATIONS

Freeman, S., "Retrospective Dynamic Transmit Focusing", Ultrasonic Imaging 17, 1995, pp. 173-196.

Gammelmark, K.L., et al. "Multi-Element Synthetic Transmit Aperture Imaging using Temporal Encoding", 2002 SPIE Medical Imaging Meeting, Ultrasonic Imaging and Signal Processing, 2002; pp. 25-36.

Haun, Mark Alden, "New Approached to Aberration Correction in Medical Ultrasound Imaging", Ph.D. Thesis, University of Illinois at Urbana-Champaign, 2003, 134 pages.

Hergum, T., et al., "Parallel Beamforming using Synthetic Transmit Beams", 2004 IEEE International Ultrasonics, Ferroelectrics, and Frequency Control Joint 50th Anniversary Conference, pp. 1401-1404.

Jellins, J. et al., "Velocity compensation in water-coupled breast echography", Ultrasonics, Sep. 1973, pp. 223-226.

Liu, D., et al., "Adaptive Ultrasonic Imaging Using SONOLINE Elegra™", 2000 IEEE Ultrasonics Symposium, 4 pages.

Nock, L., et al., "Phase aberration correction in medical ultrasound using speckle brightness as a quality factor", J. Acous. Soc. Am., May 1989, vol. 85, No. 5, pp. 1819-1833.

Robinson, B., et al., "Synthetic Dynamic Transmit Focus", 2000 IEEE Ultrasonics Symposium, pp. 1209-1214.

International Search Report and Written Opinion dated Apr. 3, 2008 for PCT Application No. PCT/US07/81253, 9 pages.

(56) References Cited

OTHER PUBLICATIONS

Office Action dated Nov. 5, 2010 for U.S. Appl. No. 12/628,169, 8 pages.
Office Action dated Aug. 3, 2010 for U.S. Appl. No. 11/586,212, 8 pages.
Office Action dated Jun. 24, 2010 for U.S. Appl. No. 11/492,471, 11 pages.
Office Action dated Oct. 27, 2009 for U.S. Appl. No. 11/492,557, 14 pages.
Notice of Allowance dated May 15, 2009 for U.S. Appl. No. 10/961,709, 8 pages.
Office Action dated Feb. 3, 2009 for U.S. Appl. No. 11/492,557, 15 pages.
Office Action dated Dec. 2, 2008 for U.S. Appl. No. 10/961,709, 4 pages.
Office Action dated Sep. 14, 2007 for U.S. Appl. No. 10/961,709, 6 pages.
Nitzpon, P., et al., "New Pulsed Wave Doppler Ultrasound System to Measure Blood Velocities Beyond the Nyquist Limit," 1995, IEEE Transactions Ultrasonics and Ferroelectrics, and Frequency Control, vol. 42, No. 2, pp. 265-279.
Tortoli, P., et al., "Velocity Profile Reconstruction Using Ultrafast Spectral Analysis of Doppler Ultrasound," IEEE Transactions Sanies and Ultrasonics, vol. SU-32, No. 2, pp. 555-561. 1985.
Office Action dated Sep. 14, 2012 for U.S. Appl. No. 12/340,578, 7 pages.
Office Action dated Jun. 6, 2013 for U.S. Appl. No. 12/340,578, 9 pages.
Office Action dated Jun. 9, 2014 for U.S. Appl. No. 12/340,578, 8 pages.
Notice of Allowance dated Feb. 17, 2015 for U.S. Appl. No. 12/340,578, 8 pages.

\* cited by examiner

SYSTEM AND METHOD FOR PROVIDING VARIABLE ULTRASOUND ARRAY PROCESSING IN A POST-STORAGE MODE

CROSS-REFERENCE TO RELATED APPLICATIONS

This application claims the benefit of U.S. patent application Ser. No. 14/748,084, filed Jun. 23, 2015 for "System and Method for Providing Variable Ultrasound Array Processing in a Post-Storage Mode," which claims the benefit of U.S. patent application Ser. No. 12/340,578, filed Dec. 19, 2008 for "System and Method for Providing Variable Ultrasound Array Processing in a Post-Storage Mode," which claims priority to U.S. Provisional Patent Application No. 61/015,632 filed Dec. 20, 2007 for "System and Method for Providing Variable Ultrasound Array Processing in a Post-Storage Mode," each of which is hereby incorporated by reference.

BACKGROUND OF THE INVENTION

The present invention relates generally to ultrasound imaging, and more specifically to imaging techniques in a post-storage mode.

The following references are incorporated by reference:
- U.S. Pat. No. 4,265,126: Papadofrangakis et al. (1981) "Measurement of true blood velocity by an ultrasound system."
- U.S. Pat. No. 4,604,697: Luthra et al. (1986) "Body imaging using vectorial addition of acoustic reflection to achieve effect of scanning beam continuously focused in range."
- U.S. Pat. No. 5,365,929: Peterson (1994) "Multiple sample volume spectral Doppler."
- U.S. Pat. No. 5,409,010: Beach et al. (1995) "Vector Doppler medical devices for velocity studies."
- U.S. Pat. No. 5,415,173: Miwa et al. (1995) "Ultrasound diagnosis system."
- U.S. Pat. No. 5,690,111: Tsujino (1995) "Ultrasound diagnostic apparatus."
- U.S. Pat. No. 6,221,020: Lysyansky et al. (2001) "System and method for providing variable ultrasound analyses in a post-storage mode."
- U.S. Pat. No. 6,263,094: Rosich et al. (2001) "Acoustic data acquisition/playback system and method."
- U.S. Pat. No. 6,450,959: Mo et al. (2002) "Ultrasound B-mode and Doppler flow imaging."
- U.S. Pat. No. 6,679,847: Robinson et al. (2004) "Synthetically focused ultrasonic diagnostic imaging system for tissue and flow imaging."
- U.S. Pat. No. 6,860,854: Robinson et al. (2005) "Synthetically focused ultrasonic diagnostic imaging system for tissue and flow imaging."
- U.S. Pat. No. 6,926,671: Azuma et al. (2005) "Ultrasonic imaging apparatus and method."
- U.S. patent application Ser. No. 11/492,471, filed Jul. 24, 2006: Napolitano et al. "Continuous Transmit Focusing Method And Apparatus For Ultrasound Imaging System."
- Tortoli et al. (1985) "Velocity profile reconstruction using ultrafast spectral analysis of Doppler ultrasound." IEEE Transactions Sonics and Ultrasonics, vol. SU-32, pp. 555-561.
- Nitzpon et al (1995) "New pulsed wave Doppler u/s system to measure blood velocities beyond the Nyquist limit." IEEE Transactions Ultrason., Ferroelec. and Freq. Cntrl., vol. UFFC-42, pp. 265-279.

In ultrasonic B-mode imaging, a two-dimensional (2D) image of tissue is created in which the echo intensity is mapped to pixel brightness. For continuous wave (CW) measurement of blood flow in the heart and vessels, the frequency shifts of backscattered ultrasound waves are used to estimate blood velocities. For pulsed wave (PW) measurement of blood flow, the phase shifts of backscattered ultrasound waves from a number of transmit excitations are used for flow estimation. In 2D color flow imaging and timeline color-M mode, the mean phase shift, which is proportional to the motion-induced Doppler frequency shift, is displayed using different colors that represent different flow speed. In spectral Doppler mode, the power spectrum of Doppler signals are computed and displayed as velocity-time waveforms. Contrast agents may be employed with any of the imaging modes to further enhance the signal-to-noise or signal-to-clutter ratio.

A typical ultrasound imaging system will include the following main subsystems: a transmitter, a receiver, a receive focusing unit, a cine memory buffer, an image processor/display controller, a display unit, and a master controller.

FIG. 1 is a block diagram of a conventional ultrasound system for which the receive array focusing unit is referred to as a beamformer, and image formation is performed on a scan-line-by-scan-line basis. System control is centered in the master controller, which accepts operator inputs through an operator interface and in turn controls the various subsystems. For each scan line, the transmitter generates a radio-frequency (RF) excitation voltage pulse waveform and applies it with appropriate timing across the transmit aperture (defined by a sub-array of active elements) to generate a focused acoustic beam along the scan line. RF echoes received by the receive aperture of the transducer are amplified and filtered by the receiver, and then fed into the beamformer, whose function is to perform dynamic receive focusing; i.e., to re-align the RF signals that originate from the same locations along various scan lines.

To reduce the data sampling rate requirements, the RF data is often converted (not shown) into baseband I/Q data before or after the beamformer. In the ZONARE z.one™ system, a synthetic array focusing approach such as shown in U.S. patent application Ser. No. 11/492,471, filed Jul. 24, 2006 for "Continuous Transmit Focusing Method And Apparatus For Ultrasound Imaging System" (David J. Napolitano et al.) is used for 2D imaging. Specifically, a complete set of echo data obtained from a sequence of transmit-receive cycles is accumulated in digital memory first, and then combined coherently in the receive focusing unit to produce the effect of having continuously focused transmit and receive beams throughout the image field. Other methods of synthetic focusing have also been described in U.S. Pat. Nos. 4,604,697, 6,679,847, and 6,860,854, for both B-mode and flow imaging.

The image processor performs the processing specific to the active imaging mode(s) including 2D scan conversion that transforms the image data from an acoustic line grid to an X-Y pixel image for display. For Spectral Doppler mode, the image processor performs wall-filtering followed by spectral analysis of Doppler-shifted signal samples using typically a sliding FFT-window. It is also responsible for generating the stereo audio signal output corresponding to forward and reverse flow signals. In cooperation with the master controller, the image processor also formats images from two or more active imaging modes, including display annotation, graphics overlays and replay of cine loops and recorded timeline data.

The cine buffer provides resident digital image storage for single image or multiple image loop review, and acts as a buffer for transfer of images to digital archival devices. On most systems, the video images at the end of the data processing path can be stored to the cine memory. In state-of-the-art systems, amplitude-detected, beamformed data may also be stored 22 in cine memory. For spectral Doppler, some machines store the wall-filtered, baseband Doppler I/Q data for the user-selected range gate in cine memory, and the ZONARE z.one system stores the pre-wall-filtered data.

U.S. Pat. No. 6,263,094 describes a system wherein raw or partially processed data acquired early in the pipeline (pre-beamformed, post-beamformed, pre-video, etc.) is stored in non-volatile memory, and can be introduced into a signal processing system from memory at least at the rate that it was acquired, to produce a real time image that can be modified by the reviewer by further processing, if desired. The strict requirement of introducing the acoustic data at least at that particular rate is to ensure the real time playback is "as if the insonified target was the source of the acoustic data, not a storage device." [4:30-31].

For motion imaging, the cost of storing Doppler data from earlier points in the receive data path is greater cine memory capacity (or shorter image loops for the same memory size) and increased post-storage processing load (and response time). The benefits are encapsulated by the concept of a "virtual patient;" i.e., the sonographer can focus on setting the probe over the region of interest, and storing the raw (i.e., unprocessed) Doppler data first. Then, during cine review, the operator can take time to re-adjust the image processing parameters based on the same data set (the "virtual patient") without keeping the patient around longer than needed. Considering the fact that sonographers need to manage many front-panel system controls with one hand, hold the probe with the other hand, and deal with the patient's body movements, the workflow and ergonomic advantages of such post-storage data processing capabilities are clear.

U.S. Pat. No. 6,221,020 describes a system wherein beamformed (I/Q or RF) data from a region of interest is accumulated 24 in cine memory during a storage period. As illustrated in FIG. 2, the receive beamforming refers to a weighted delay-and-sum operation, and the amplitude weighting across receive aperture is referred to as "apodization," which is important for suppressing the sidelobes of the receive beam profile. This method enables, during post-storage playback operation, any known signal processing and system control which have conventionally been carried out in real-time during the scanning session. For example, in a playback mode, the user may select any scan line and Doppler gate location and width within the region of interest for spectral Doppler or for color M-mode analysis. However, a limitation of this prior art is that the post-storage processing capabilities are restricted to conventional methods based on ultrasound data that is already beamformed.

Due to patient-to-patient variations and different anatomical scenarios in different clinical applications, a number of important system controls actually need to be effected before or during the beamforming process. For example, it is well known that the sound speed parameter used for array focusing operations can vary with different organ types and from patient to patient. Any sound speed optimization must be performed during the receive array focusing or reconstruction process. In particular, the ZONARE z.one system supports channel domain processing that first stores all the raw transducer element data in a channel domain memory, and then allows digital signal processor units to access the channel data multiple times in order to support an iterative algorithm that optimizes the array focusing sound speed. It is important to note that this kind of adaptive processing may take up to a few seconds to complete while the rest of the signal pipeline is paused; i.e., the channel data is often read out by the signal processors multiple times and at a rate that may be lower than when it was acquired.

In spectral Doppler mode, the receive aperture, which determines the receive F-number (defined by the ratio of focal range to aperture size), directly controls the degree of receive focusing. A lower F-number means stronger focusing or a tighter beam width. For small vessels or weak signals from deep lying vessels, it is advantageous to maximize the receive aperture size for best sensitivity/penetration. On the other hand, it is well known that because different elements of the active aperture form different angles with the flow direction, a large aperture (low F-number) can give rise to an increased velocity over-estimation errors—an effect referred to as geometrical spectral broadening.

U.S. Pat. No. 6,679,847 describes the synthetic focus system that stores raw channel data and applies different beamforming delay curves to track blood motion. This invention is also aimed at providing flexible motion analyses and display methods, but it is fundamentally a pure synthetic focus system that utilizes single or small groups of elements for transmit (with known sensitivity challenges associated with limited acoustic power outputs) and requires an entire set of uncombined channel data to be stored for each image frame.

SUMMARY OF THE INVENTION

There is a need for a more flexible system that can store data that is not fully beamformed, and can introduce the stored data into a signal processing unit at a suitable rate that is not bound by the acquisition data rate, to provide variable Doppler array focusing adjustments and image processing in a post-storage mode.

The present invention pertains to novel imaging capabilities in a post-storage mode, and is typically incorporated in an ultrasound imaging system that includes the following main subsystems: a transmitter, a receiver, a receive focusing unit, a cine memory buffer, an image processor/display controller, a display unit and a master controller.

Embodiments of the present invention provide a system and method for accumulating partially reconstructed echo data from a region of interest during a storage period. The selection of the region of interest may be effected via standard user interface control mechanisms (e.g. trackball and "set" buttons), based on a real-time background B-mode and/or color flow image display. The accumulated echo data representing the region of interest is then processed during a post-storage operation to provide a number of user-selectable and/or adaptive array focusing strategies, motion analysis and display modes. The system further comprises front-panel controls that enable the user to select not only which retrospective processing method to be used, but also one or more spatial locations within the region of interest for such processing.

The techniques for accumulating partially reconstructed echo data from a region of interest during the storage period (where results are stored for subsequent processing in the post-storage phase) represent a commercially significant body of technology in their own right. Similarly, the techniques for retrieving and processing the partially reconstructed data during the post-storage period represent a commercially significant body of technology in their own right. Thus the two, which may be thought of as sub-combinations, should each be seen as a standalone aspect of the invention. While by definition accumulation and processing are done at different times, it is also contemplated that the two will often be done in different places by different entities.

In addition to the post-storage array focusing and image processing parameter adjustments, a number of advanced Doppler analysis and imaging methods can benefit from this invention include Doppler spatial compounding for improved velocity estimation, dual-frequency Doppler for extended velocity range, dual timeline Doppler, multi-gate spectral flow imaging, strain-rate imaging and adaptive post-processing including adaptive clutter filtering and display parameters. These and other methods have been reported in various published papers and are well known to those skilled in the art.

Hence, the potential benefits of this invention include not just all of the virtual patient capabilities, but also being able to analyze and process the same Doppler data using alternate processing and display methods aimed at extracting more diagnostic information.

A further understanding of the nature and advantages of the present invention may be realized by reference to the remaining portions of the specification and the drawings.

DESCRIPTION OF SPECIFIC EMBODIMENTS

Figure 3:
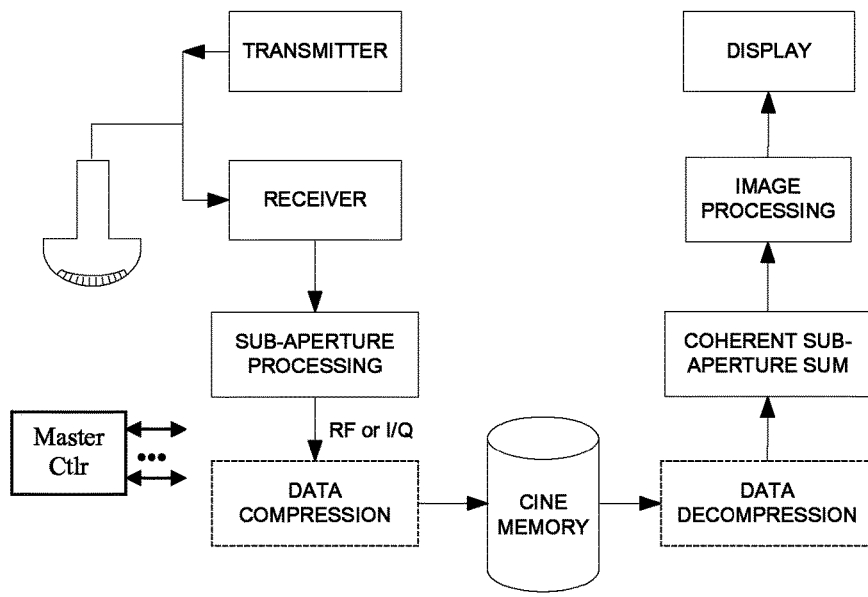
FIG. 3 is a block diagram of a specific embodiment of the present invention.

FIG. 3 is a block diagram of a preferred embodiment of the present invention for which system control is centered in a master controller that accepts operator inputs through an operator interface and in turn controls the various major data processing subsystems. It is well known to those skilled in the art that, through a user interface, the operator can specify a region of interest ("ROI") for a motion imaging mode (e.g., spectral Doppler, color velocity and energy imaging, and Doppler tissue imaging) within a background B-mode image. It is also well known that depending on the transducer type (curvilinear, linear or sector), a corresponding scan format is used to generate both the B-mode and motion imaging ROI.

Figure 4:
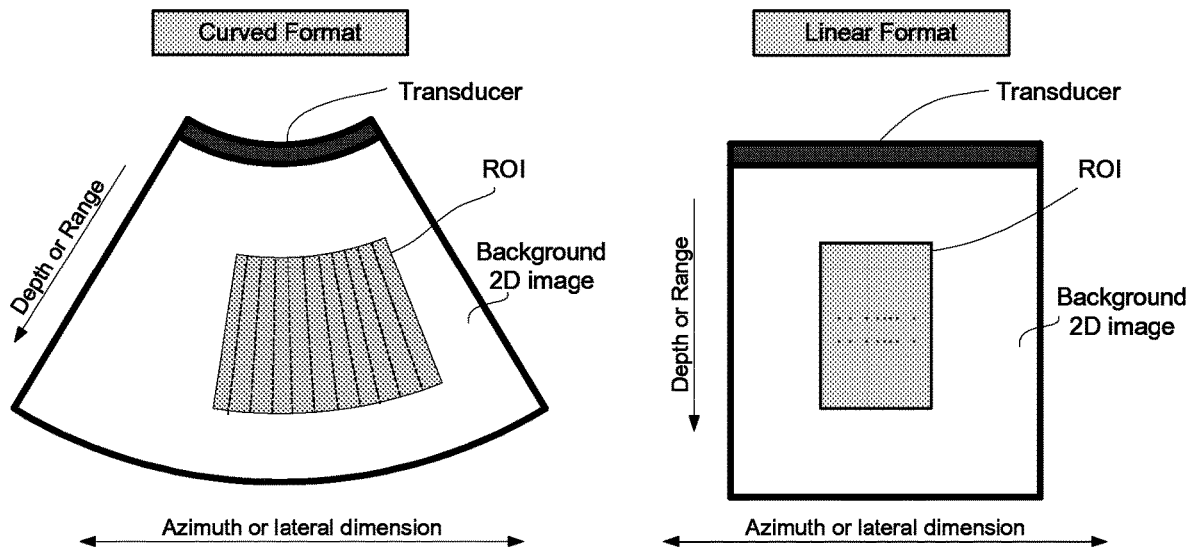
FIG. 4 shows a preferred embodiment showing a motion imaging region of interest ("ROI") for a curved scan format (left portion of figure) and for a steered linear scan format (right portion of figure)

FIG. 4 shows the examples of a curved and a linear array PW scan format, wherein the 2D motion imaging ROI defines a 2D acoustic grid for array focusing or reconstruction operations. If the reconstruction is achieved using a conventional beamforming method, the acoustic grid comprises a set of scan lines as illustrated for the case of the curvilinear scan. With ZONARE's imaging approach (see U.S. patent application Ser. No. 11/492,471), the received data from all receive channels and transmit events are first accumulated into a channel domain memory unit (not shown), such that the array focusing can follow an arbitrary acoustic grid as illustrated for the case of the linear scan (notice the lateral and/or axial spacing do not even need to be uniform). In general, the transmit-receive array focusing and steering strategies including the acoustic reconstruction grid are independent of those that constitute the background 2D image.

In general, this invention can be extended to 3D imaging such that the ROI refers to a 3D volume in space. That is, the ROI is not restricted to a 2D plane as shown in FIG. 4. For CW Doppler imaging, the ROI would theoretically extend from the surface of the probe to infinite depth.

Transmitter and Receiver

The main functions of the transmitter and receiver in FIG. 3 are to acquire a set of echo data from the ROI over a sufficiently long time interval such that motion effects can be measured. For both CW and PW imaging modes, the ROI can be divided into one or more transmit scan directions, and it is well known that the overall lateral spatial resolution is determined by the product of the transmit and receive array focusing response at each location.

In PW modes, a number of repeated transmit-receive events at a user-selectable pulse repetition frequency (PRF) is used to interrogate moving sound reflectors along each transmit scan direction. That is, for each spatial location within the ROI, a packet of echo data samples from the repeated transmit-receive events is available for analysis. The number of data samples per packet is referred to as a "packet size." For each packet, motion-induced echo changes from one sample to the next can be detected. A motion estimate (e.g., mean velocity) can be derived for each spatial location within the ROI, and the results can be translated into a 2D image, usually via a color mapping.

Suppose the ROI consists of 10 scan directions and suppose the packet size is 12. This means that for each image frame, 10×12=120 transmit-receive events are needed. In order to maximize the data acquisition time, various well known acquisition strategies may be used including multi-line and broad beam acquisition (one transmit broad beam spans two or more lateral positions in the acoustic reconstruction grid) and transmit interleaving (when the PRF is sufficient low such as for deep imaging, a transmit pulse may be fired along a different scan direction before the echo from the previous firing returns). Typically, the RF echoes received by the receive aperture of the transducer are amplified and filtered by the receiver.

To enhance the axial resolution of the transmit pulse, and/or improve penetration, coded excitation methods may be used wherein the transmit encoder (not shown) repeats a transmit pulse multiple times according to a signal modulation or coding scheme and a receive decoder (not shown) compresses the received signal thereby restores the uncoded pulse resolution but with greater signal to noise ratio. It is well known to those skilled in the art that the receive decoding can be implemented before or after receive array focusing.

To reduce the data sampling rate requirements, the RF echo data is often converted (not shown) into baseband I/Q data before or after receive beamforming or array focusing. Optionally, as in the ZONARE z.one system, the received data from all receive channels and transmit events can be accumulated into a channel domain memory unit first prior to sub-aperture processing. Throughout this document, the term "image reconstruction" will be used in relation to the preferred embodiments of the present invention, as the channel domain processing involved is different and more general than conventional beamforming.

Sub-Aperture Processing

Figure 1:
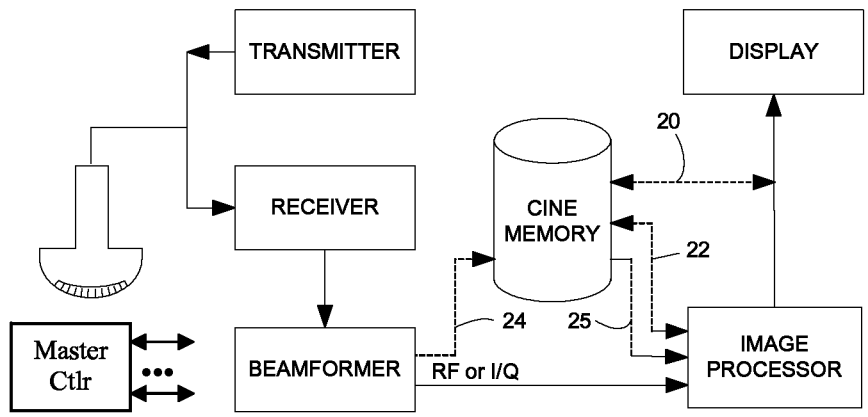
FIG. 1 is a block diagram of a conventional ultrasound system.
Figure 2:
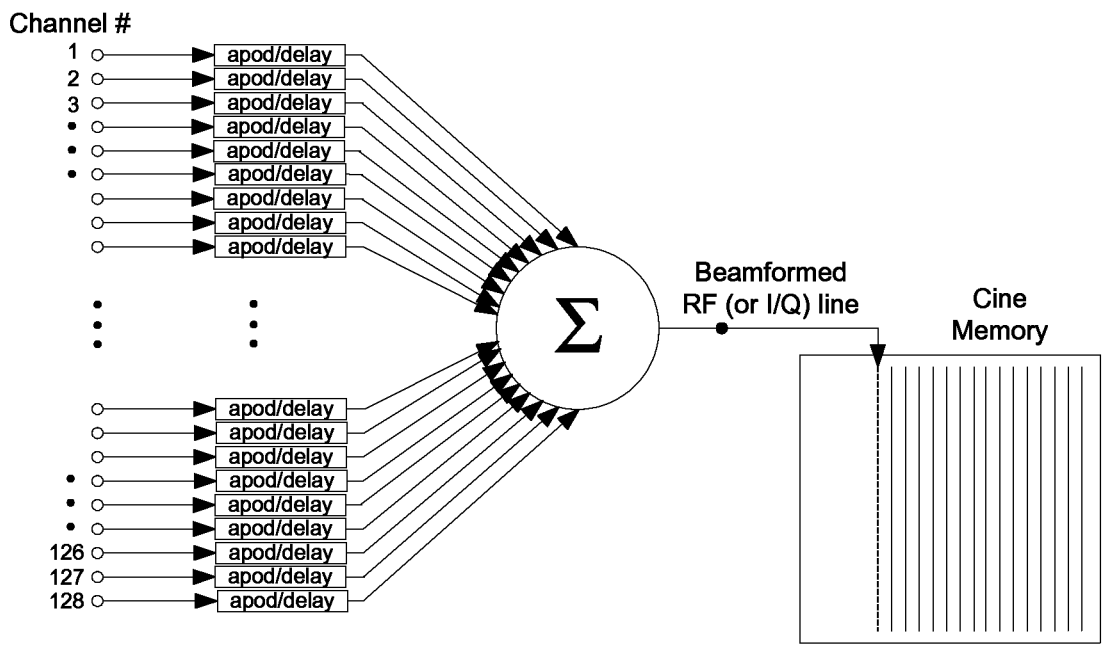
FIG. 2 is a block diagram showing prior art receive beamforming where a weighted delay-and-sum operation is performed.

In contrast to the prior art of FIG. 2, an important aspect of the present invention lies with the sub-aperture processing of the received echo data from the different elements of the receive aperture. A sub-aperture refers to any subset (i.e., not necessarily contiguous) of the transducer elements that comprise the full receive aperture. For example, a sub-aperture may be defined by alternating elements across the physical array, or by alternating groups of 2 or more elements. The partially focused sub-aperture data sets are then stored in the cine memory such that during a post-storage period, the user can process and re-process the stored data with new degrees of flexibility not available with conventional systems. "Subset" in this context means at least one transducer element and fewer than all the transducer elements.

Figure 5:
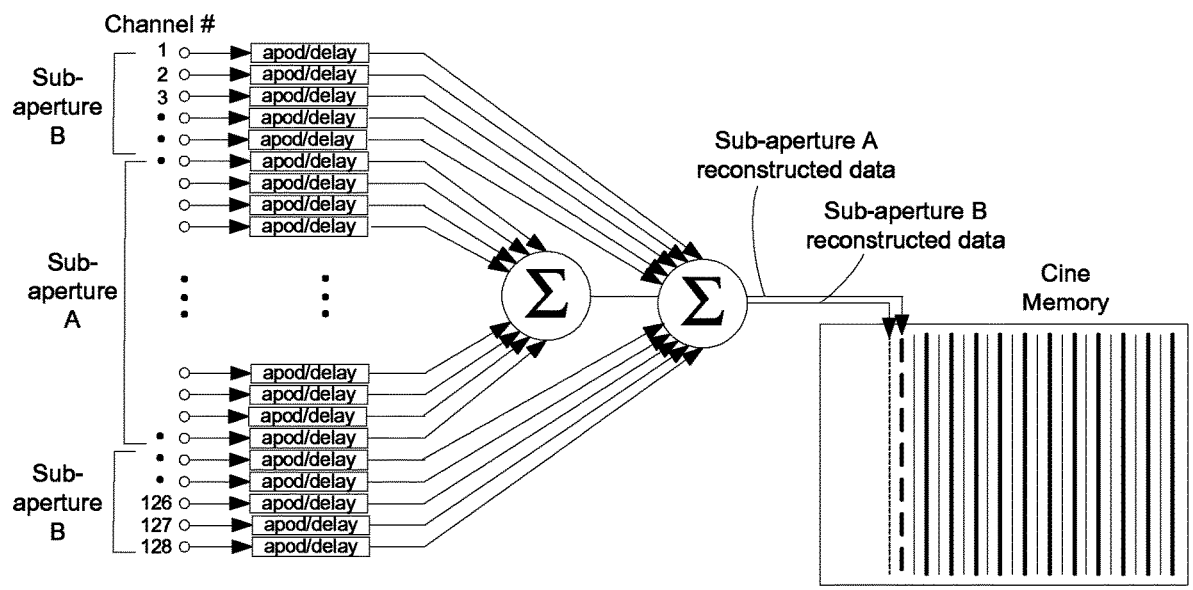
FIG. 5 shows a preferred embodiment in which the two receive sub-aperture channel sets are reconstructed and stored for each acoustic grid point.

As illustrated by FIG. 5, one preferred embodiment is to divide the receive aperture into two groups: an inner sub-aperture group (A) and an outer sub-aperture group (B). Each group is combined taking into account of time delay, phase and amplitude weighting for optimal receive focusing. During post-storage processing, the receive aperture can effectively be adjusted by applying different weightings to the inner and outer sub-aperture. For flow imaging, this provides a means for the user to adjust the tradeoff between flow sensitivity and geometrical spectral broadening error.

Figure 6:
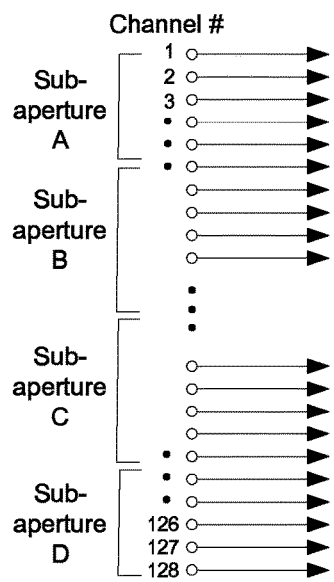
FIG. 6 shows a preferred embodiment in which the receive channels are divided into four sub-aperture groups for processing and storage.

In another preferred embodiment as shown in FIG. 6, the receive channels are grouped into a set of N contiguous sets of receive aperture elements. For example, suppose there are N=4 channels groups of different aperture sizes. For each acoustic grid point, 4 groups of partial reconstruction (apodized coherent sums) will be stored. A coarse sound speed tuning can be realized by adjusting the relative time delays of the different sub-aperture groups during post-storage processing. That is, each sub-aperture group is regarded as a single receiver whose time delay is given by twice the distance between the center of the sub-aperture to the desired focus location, divided by an assumed sound speed value. This process can also be automated by implementing an iterative algorithm in the image processor that combines (with appropriate time delays) the sub-aperture data set multiple times using a range of trial sound speed values, and automatically selects the best sound speed that yields the best focusing in terms of a pre-determined metric (e.g., signal energy within the focus region).

As disclosed separately in U.S. patent application Ser. No. 11/492,471, reconstruction (sub-aperture reconstruction in the present case) is not limited to receive array focusing, but may incorporate synthetic transmit array focusing, especially for slow flow conditions. That is, improvements in transmit array focusing can be achieved retrospectively by coherently combining channel data acquired from different transmit events.

Data Compression and Storage

Referring to FIG. 3, after the sub-aperture processing, the partially focused sub-aperture echo data can be optionally compressed via a suitable encoding method to reduce the total amount of data for cine memory storage. During cine playback or post-storage processing, the compressed data is first decoded or un-compressed prior to further processing. Since ultrasound echo data is correlated across channels, across range, and across spatially adjacent transmit firings, and in addition, in applications of color flow and spectral Doppler, the same reconstruction line is repeatedly sampled, there is a lot of redundant information present in raw echo data such that the opportunity for compression is great. Many encoding/decoding techniques, both lossless and lossy, can be used including simple decimation, linear predictive coding, discrete cosine transform, and wavelet transform. Some of these methods treat the data as a sequence of one's and zero's.

In a preferred embodiment of the present invention, the cine data is stored in non-volatile media on the system. In another preferred embodiment, the cine data, with or without compression, can be transferred to a remote workstation for post-processing and review. The data communications network connection to the remote review station can be a wireless network.

Preferred Embodiments of Post-Storage Variable Array Processing and Imaging Modes One preferred embodiment of the present invention pertains to post-storage CW Doppler imaging capabilities. A single transmit broad beam is used to define a relatively narrow ROI that may comprise two or more reconstruction lines as defined by receive array focusing. Since only one transmit beam is needed to scan the entire ROI, a CW transmit beam can be used, and partially focused sub-aperture receive channel groups of sampled I/Q data are stored in the cine memory. As an example, for a CW transmit frequency of $f_0$=5 MHz, if the highest blood velocity to be measured is v=10 m/s (e.g., in cardiac scans), the corresponding maximum Doppler frequency shift is 2(v/c)=64.9 kHz for c=1540 m/2 (sound speed in blood). Hence, to avoid aliasing the I/Q data may be sampled at 100 kHz. During cine playback, the user can select via front-panel control of the system a specific CW Doppler line within the ROI for spectral analysis. In effect, the CW Doppler line can be adjusted retrospectively after the raw data is acquired. Further, depending on which sub-aperture grouping method is used (FIG. 5 and FIG. 6), this invention also enables post-storage user-adjustments of receive aperture (geometrical spectral broadening errors) and receive aperture focusing sound speed.

Figure 7:
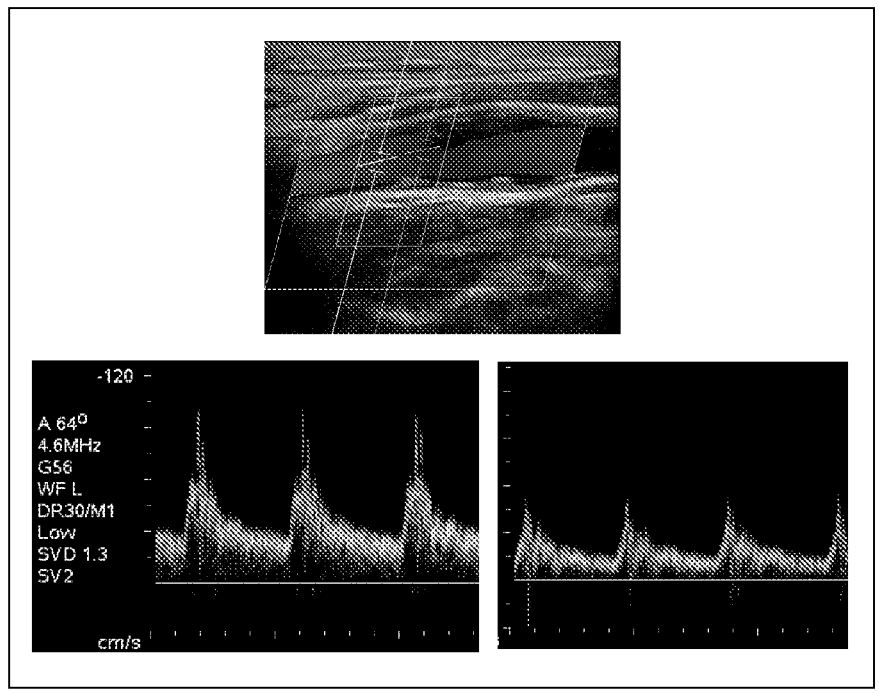
FIG. 7 shows a preferred embodiment in which the region of interest (smaller box) for which partially beamformed PW Doppler data is stored is a sub-region of the standard color flow region of interest (larger box), and also shows the time-line spectrograms for two Doppler sample volumes along separate PW Doppler lines being displayed side-by-side.

In another preferred embodiment of the present invention, a post-storage PW Doppler mode wherein the sample gate position and/or receive aperture size can be retrospectively adjusted upon cine playback. One or more transmit beams are used to define a ROI within which a specific sample gate can be selected retrospectively for spectral analysis. If the PRF is sufficiently low, two or more PW transmit-receive cycles can be interleaved; i.e., the PW transmit pulse for an adjacent beam can be fired while waiting for the echo to return from the previous firing. If the PRF is too high for interleaving, a single and broader transmit beam may be used such that it covers the entire ROI. The received channel data for each transmit firing are grouped according to the inner and outer sub-aperture scheme of FIG. 5, with each group combined to form two or more reconstruction lines that span the ROI, and then stored in cine memory. Upon cine playback, any sample gate along any reconstruction line within the ROI can be selected via front-panel controls for spectral Doppler analysis as in live PW spectral Doppler imaging. One exemplary application is, as shown in FIG. 7, is to enable comparative and/or simultaneous blood flow analysis at two different locations relative to a stenosis in an artery. Two independent sample gates along two different reconstruction lines can be selected for spectral analysis, and the resultant time-line spectral waveforms can be displayed as a dual-image below the 2D color flow reference image. Regardless of the post-processing and display method, the receive aperture size for a selected PW Doppler line can be adjusted by applying different weight factors to the partially focused inner and outer sub-aperture echo data.

Figure 8:
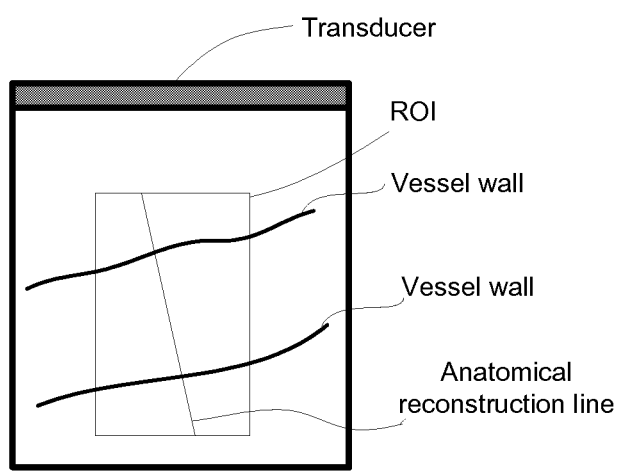
FIG. 8 shows an anatomical reconstruction line within the ROI.

In another preferred embodiment, one or more transmit PW broad beams are used to define the ROI. The received channel data for all transmit events are accumulated in a channel domain memory. With access to the channel data memory, programmable processors (e.g., DSP chips, FPGA) are employed to perform the sub-aperture reconstruction, which is no longer constrained to follow a set of scan lines as in a conventional hardware-based beamformer. As illustrated in FIG. 8, the reconstruction follows an "anatomical line" that can be specified via front-panel user-controls to be substantially normal to the near and far walls of a vessel of interest, instead of a conventional scan line that is parallel to the transmit-receive beam. In general, an anatomical reconstruction line is chosen to follow the geometry of the anatomy of interest (e.g., vessel cross-section) instead of a transmit-receive beam pattern. During cine playback, the user can select any arbitrary sample gate along the anatomical reconstruction line for detailed spectral analysis. Alternatively, a plurality of sample gates along a selected anatomical line can be processed in parallel to produce a dynamic spectral flow profile of range versus velocity, as taught by Tortoli et al. (1985), and also taught in U.S. Pat. No. 6,450,959.

Figure 9:
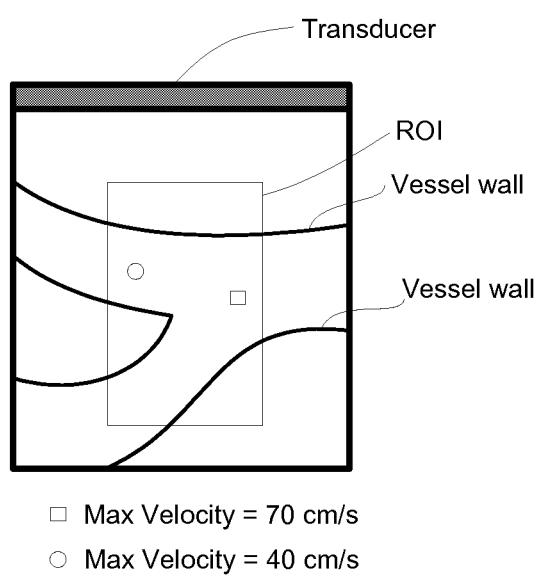
FIG. 9 shows multiple sample volumes for quantitative Doppler waveform analysis.

As an extension to the preferred embodiments of FIG. 7 and FIG. 8, the user can select two or more sample volumes in arbitrary positions within the ROI for quantitative spectral Doppler waveform index calculations during a post-storage period. Shown in FIG. 9 is an example in which a bifurcating artery is being studied by placing a sample volume in the common vessel and one in a branch vessel. The time-line spectral Doppler waveforms corresponding to the two sample volumes can be optionally displayed as a dual image below the 2D image (as in FIG. 7). An automated maximum envelope or mean velocity waveform tracing algorithm is implemented to track various spectral waveform indices such as maximum velocity (over a cardiac cycle) and the systolic to diastolic ratio. In FIG. 9, the maximum velocities for the two sample volumes are displayed below the 2D image.

Another preferred embodiment of the present invention is retrospective 2D color flow or tissue motion imaging. The acquisition strategies and options are similar to the aforementioned PW Doppler modes, except the display is in the form of a colorized flow image or a 2D grid of sample gates within the ROI. A packet of say, 10 transmit-receive events is acquired for each motion image frame, and another packet for the next frame etc. For each image frame, a 2D grid of sample gates is analyzed serially or in parallel to estimate motion parameters such as mean velocity and motion signal energy. The processing may include a motion-discrimination filtering step including a high-pass "clutter" filter for flow imaging, and a low-pass "flow-signal" filter for tissue motion imaging. The results are displayed using a predetermined color map to provide a visual representation of the spatial distribution of the flow parameters within the ROI.

Another preferred embodiment of the present invention involves use of two or more independent sets of reconstruction lines that intersect each other within the ROI. It is well known to those skilled in the art that sub-aperture data obtained from two or more independent views of a sample volume can be combined to estimate the velocity vector (magnitude and direction) and/or to reduce estimation variance. By storing the sub-aperture data sets corresponding to different reconstruction lines in cine memory, the improved velocity estimation can be effected in a post-storage mode.

Other advanced Doppler analysis and imaging methods that can benefit from the present invention include dual-frequency Doppler for extended unambiguous velocity measurement range, and adaptive post-processing including adaptive receive aperture, range-gating, PRF re-sampling, and display parameters. For example, using the inner and outer sub-aperture method of FIG. 5, an adaptive receive aperture can be realized by prescribing weight factors for the two sub-aperture groups based on an estimate of the motion signal parameter (e.g., signal energy, mean or maximum Doppler frequency). If the flow signal is strong, the weighting on the outer sub-aperture group may be reduced relative to the inner sub-aperture group thereby reduce geometrical spectral broadening errors.

In the foregoing specification the invention has been described with reference to specific exemplary embodiments. It will, however, be evident that various modifications and changes can be made without departing from the broader spirit and scope of the invention as set forth in the appended claims. The specification and drawings are, accordingly, to be regarded in an illustrative rather than restrictive sense.

The invention claimed is:
1. A method of analyzing movement within a region of interest comprising:
 activating at least a portion of a multi-element transducer array to transmit, at once, a single ultrasonic broad beam that can scan an entire region of interest through a transmit aperture along one or more scan directions that span the region of interest;
 receiving, by one or more elements in the multi-element transducer array, ultrasound echoes through a receive aperture;
 grouping echo data received by the one or more elements into at least one of a first sub-aperture data set and a second sub-aperture data set, wherein the first sub-aperture data set includes the echo data related to first sub-aperture and the second sub-aperture data set includes the echo data related to second sub-aperture, wherein the first sub-aperture is different from the second sub-aperture, the first sub-aperture data set is different from the second sub-aperture data set, the first sub-aperture data set and the second sub-aperture data set correspond to all ultrasound echoes of the single ultrasonic broad beam;
 coherently combining the echo data grouped into the first sub-aperture data set based on both phase and ampli- tude of the echo data grouped into the first sub-aperture data set to generate a first partially focused data set representing a first portion of the region of interest, wherein the first partially focused data set is used for generating part of an image for one or more reconstruction lines;

coherently combining the echo data grouped into the second sub-aperture data set based on both phase and amplitude of the echo data grouped into the second sub-aperture data set to generate a second partially focused data set representing a second portion of the region of interest, wherein the second partially focused data set is used for generating another part of the image for one or more reconstruction lines;

storing the first partially focused data set and the second partially focused data set during a storage period in a format that can be retrieved for later analysis; and generating the image for one or more reconstruction lines based on a combination of the first partially focused data set and the second partially focused data set.

2. The method of claim 1, further comprising:

during a post-storage period, retrieving sub-aperture data from stored sub-aperture data sets at a rate independent of an acquisition rate of the sub-aperture data;

combining the sub-aperture data to form one or more selected reconstruction lines;

processing the sub-aperture data to extract motion information from one or more sample positions along the selected reconstruction lines; and displaying an image representative of the motion information.

3. The method of claim 1, further comprising: selecting, in response to user signals, one or more spatial locations within the region of interest for retrospective processing during a post-storage period;

adjusting, in response to user signals, the post-storage receive array focusing and motion-analysis modes, including a 2D quantitative flow mapping, and associated processing parameters including one or more clutter filter parameters or image display parameters.

4. The method of claim 1, wherein the one or more ultrasonic beams comprises a sequence of ultrasound pulses designed to adequately sample a moving target, including blood, with a given maximum velocity in the direction of the one or more ultrasonic beams.

5. The method of claim 1, wherein each ultrasonic beam comprises a continuous acoustic wave of a predetermined transmit frequency.

6. The method of claim 1, wherein the one or more ultrasonic beams include at least two beams that cross over each other within the region of interest.

7. The method of claim 1, wherein the ultrasound echoes are converted from radio frequency (RF) signals to baseband I/O components prior to storage.

8. The method of claim 1, wherein the ultrasound echoes for each transmit event is accumulated and stored in a channel domain memory until partial focusing operations for an entire image frame are completed.

9. The method of claim 1, further comprising:

performing partial focusing operations by combining echo data obtained from two or more transmit events to synthesize or improve an effective transmit array focusing.

10. The method of claim 1, wherein the first sub-aperture data set and the second sub-aperture data set form a receive aperture data set for the receive aperture, wherein the receive aperture data set is divided into two channel groups including an inner group that represents signals received by an inner sub-group of elements in the multi-element transducer array, and an outer group that represents signals received by elements positioned on each side of the inner sub-group of elements in the multi-element transducer array.

11. The method of claim 1, wherein the receive aperture is divided into N contiguous groups of elements, where N is greater than or equal to two.

12. The method of claim 1, wherein the one or more reconstruction lines include any locus of reconstruction points that follows an anatomy of interest, including at least one of a blood vessel or a cross-section, within the region of interest independent of the one or more scan directions.

13. The method of claim 1, wherein each sub-aperture data set is combined with appropriate time delays, phase shifts and amplitude weightings to form partially focused lines along the one or more reconstruction lines prior to storage.

14. The method of claim 1, wherein the first partially focused data set and the second partially focused data set are stored in non-volatile media on a system or on a remote review station that is connected to the system via a digital communications network.

15. The method of claim 1, wherein, during a post-storage period, the first partially focused data set and the second partially focused data set are combined with different respective amplitude weightings as part of applying a first weight factor and a second weight factor to the first partially focused data set and the second partially focused data set to control an aperture apodization function used to generate the image for the one or more reconstruction lines.

16. The method of claim 1, further comprising:

determining a first sound speed for a pre-determined metric by iteratively adjusting the first partially focused data set based on a plurality of trial sound speed values;

determining a second sound speed for the pre-determined metric by iteratively adjusting the second partially focused data set based on the plurality of trial sound speed values; and generating the image for the one or more reconstruction lines based on the first partially focused data set weighted using the first sound speed and the second partially focused data set weighted using the second sound speed.

17. The method of claim 1, wherein the received echo data is converted from RF to baseband I/Q components prior to storage.

18. A system for analyzing movement within a region of interest comprising:

a processing device; and a storage device:

the processing device, during a storage period, is operable to:

activate at least a portion of a multi-element transducer array to transmit, at once, a single ultrasonic broad beam that can scan an entire region of interest through a transmit aperture along one or more scan directions that span the region of interest;

receive, by one or more elements in the multi-element transducer array, ultrasound echoes through a receive aperture;

group echo data received by the one or more elements into at least one of a first sub-aperture data set and a second sub-aperture data set, wherein the first sub-aperture data set includes the echo data related to an inner sub-aperture and the second sub-aperture data set includes the echo data related to an outer sub-aperture, wherein the inner sub-aperture is different from the outer sub-aperture, the first sub-aperture data set is different from the second sub-aperture data set, the first sub-aperture data set and the second sub-aperture data set correspond to all ultrasound echoes of the single ultrasonic broad beam;

coherently combine the echo data grouped into the first sub-aperture data set based on both phase and amplitude of the echo data grouped into the first sub-aperture data set to generate a first partially focused data set representing a first portion of the region of interest, wherein the first partially focused data set is used for generating part of an image for one or more reconstruction lines;

coherently combine the echo data grouped into the second sub-aperture data set based on both phase and amplitude of the echo data grouped into the second sub-aperture data set to generate a second partially focused data set representing a second portion of the region of interest, wherein the second partially focused data set is used for generating another part of the image for one or more reconstruction lines;

store the first partially focused data set and the second partially focused data set during a storage period in a format that can be retrieved for later analysis; and generate the image for one or more reconstruction lines based on a combination of the first partially focused data set and the second partially focused data set.

19. A method of analyzing movement within a region of interest, comprising:

retrieving sub-aperture data generated during a previous storage period, the sub-aperture data including a first partially focused data set that represents signals received by an inner sub-aperture group of elements in a multi-element transducer array and a second partially focused data set from an outer sub-aperture group of elements in the multi-element transducer array, wherein the inner sub-aperture is different from the outer sub-aperture, the first sub-aperture data set is different from the second sub-aperture data set, the first sub-aperture data set and the second sub-aperture data set correspond to all ultrasound echoes of a single ultrasonic broad beam, wherein the first partially focused data set representing a first portion of the region of interest is formed by coherently combining echo data and is used for generating a first part of an image for one or more reconstruction lines, received by the inner sub-aperture group of elements, based on both phase and amplitude and the second partially focused data set representing a second portion of the region of interest is formed by combining echo data and is used for generating a second part of the image for one or more reconstruction lines, received by the outer sub-aperture group of elements, based on both phase and amplitude, wherein the echo data is formed by receiving a single ultrasonic broad beam that can scan an entire region of interest transmitted, at once, by at least a portion of a multi-element transducer through a transmit aperture along one or more scan directions that span the region of interest;

combining the sub-aperture data for the first partially focused data set and the second partially focused data set to form one or more reconstruction lines;

processing sub-aperture data from at least one of the first partially focused data set and the second partially focused data set that corresponds to one or more sample positions along the one or more reconstruction lines to extract motion information; and displaying the image representative of the motion information.

20. A method of analyzing movement within a region of interest comprising:

activating at least a portion of a multi-element transducer array to transmit, at once, a single ultrasonic broad beam that can scan an entire region of interest through a transmit aperture along one or more scan directions that span the region of interest;

receiving, by one or more elements in the multi-element transducer array, ultrasound echoes through a receive aperture;

grouping echo data received by the one or more elements into at least one of a first sub-aperture data set and a second sub-aperture data set, wherein the first sub-aperture data set includes the echo data related to an inner sub-aperture and the second sub-aperture data set includes the echo data related to an outer sub-aperture, wherein the inner sub-aperture is different from the outer sub-aperture, the first sub-aperture data set is different from the second sub-aperture data set, the first sub-aperture data set and the second sub-aperture data set correspond to all ultrasound echoes of the single ultrasonic broad beam;

coherently combining the echo data grouped into the first sub-aperture data set to generate a first partially focused data set representing a first portion of the region of interest, wherein the first partially focused data set is used for generating part of an image for one or more reconstruction lines;

coherently combining the echo data grouped into the second sub-aperture data set to generate a second partially focused data set representing a second portion of the region of interest, wherein the second partially focused data set is used for generating another part of the image for one or more reconstruction lines;

storing the first partially focused data set and the second partially focused data set during a storage period in a format that can be retrieved for later analysis; and generating the image for one or more reconstruction lines based on a combination of the first partially focused data set and the second partially focused data set.

* * * * *